(12) United States Patent
Herbrich et al.

(10) Patent No.: US 8,191,555 B2
(45) Date of Patent: Jun. 5, 2012

(54) INHALATION UNIT

(75) Inventors: Ernst Herbrich, Selb (DE); Otto Hampl, Hirschaid (DE); Norbert Pieper, Selb (DE)

(73) Assignee: Vishay Electronic GmbH, Selb (DE)

( * ) Notice: Subject to any disclaimer, the term of this patent is extended or adjusted under 35 U.S.C. 154(b) by 987 days.

(21) Appl. No.: 11/722,117

(22) PCT Filed: Dec. 16, 2005

(86) PCT No.: PCT/EP2005/013599
§ 371 (c)(1),
(2), (4) Date: Aug. 2, 2007

(87) PCT Pub. No.: WO2006/069650
PCT Pub. Date: Jul. 6, 2006

(65) Prior Publication Data
US 2009/0095312 A1    Apr. 16, 2009

(30) Foreign Application Priority Data
Dec. 22, 2004   (DE) .................. 10 2004 061 883

(51) Int. Cl.
*A24F 47/00*   (2006.01)
(52) U.S. Cl. ......... 131/273; 131/329; 131/194; 131/271
(58) Field of Classification Search .................. None
See application file for complete search history.

(56) References Cited

U.S. PATENT DOCUMENTS

| | | | |
|---|---|---|---|
| 4,947,874 A | 8/1990 | Brooks et al. | |
| 5,144,962 A * | 9/1992 | Counts et al. | 131/194 |
| 5,878,752 A | 3/1999 | Adams et al. | |
| 6,125,853 A | 10/2000 | Susa et al. | |
| 6,637,264 B2 * | 10/2003 | Lotters et al. | 73/204.27 |
| 2003/0132219 A1 | 7/2003 | Cox et al. | |
| 2006/0118128 A1 * | 6/2006 | Hoffmann et al. | 131/271 |

FOREIGN PATENT DOCUMENTS
DE    29604359    6/1996
(Continued)

OTHER PUBLICATIONS
Application No. 102004061883.6, Country: DE, Date of Filing: Dec. 22, 2004.*
(Continued)

*Primary Examiner* — Richard Crispino
*Assistant Examiner* — Phu Nguyen
(74) *Attorney, Agent, or Firm* — Douglas W. Sprinkle

(57) ABSTRACT

The invention relates to a heating device (9), for a mobile inhalation unit for the inhalation of active agents, comprising a heating wire (15), with two connector ends (23, 31) for the introduction of electrical energy and a thermal reservoir (13, 17) for heating air flowing along the thermal reservoir, whereby the thermal reservoir may be heated by means of the heating wire. The heating wire has a temperature coefficient of at least 0.001 K$^{-1}$. The invention further relates to an inhalation unit with such a heating device and a method for heating a thermal reservoir on such a heating device.

19 Claims, 4 Drawing Sheets

FOREIGN PATENT DOCUMENTS

| | | |
|---|---|---|
| DE | 10212045 | 10/2003 |
| EP | 0 430 559 | 6/1991 |
| EP | 0430559 | 6/1991 |
| JP | 02-124082 | 5/1990 |
| WO | WO97/48295 | 12/1997 |
| WO | WO-03/012565 | 2/2003 |
| WO | WO-2004/098324 | 11/2004 |

OTHER PUBLICATIONS

Notification of Transmittal of Translation of the International Preliminary Report an Patentability (Chapter I or Chapter Ii of the Patent Cooperation Treaty) PCT/EP2005/013599 dated Nov. 15, 2007.

Japanese Office Action date May 31, 2011. JP application 2007-547301.

* cited by examiner

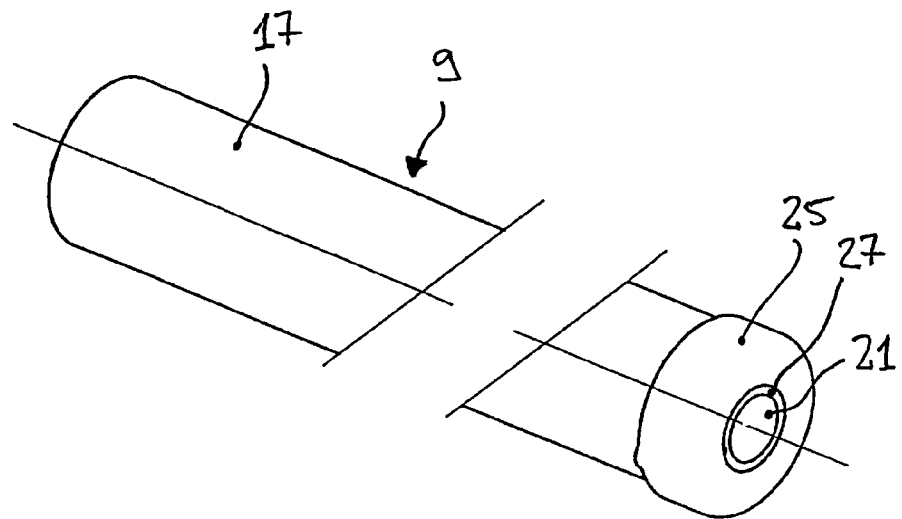
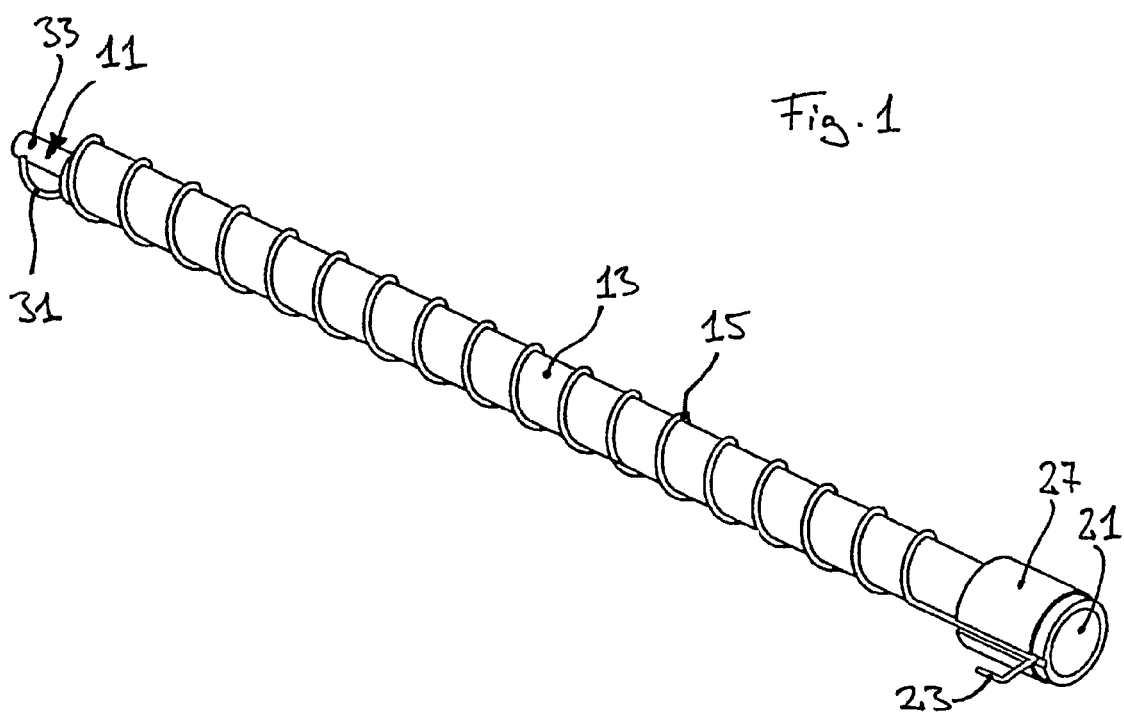
Fig. 1
Fig. 2

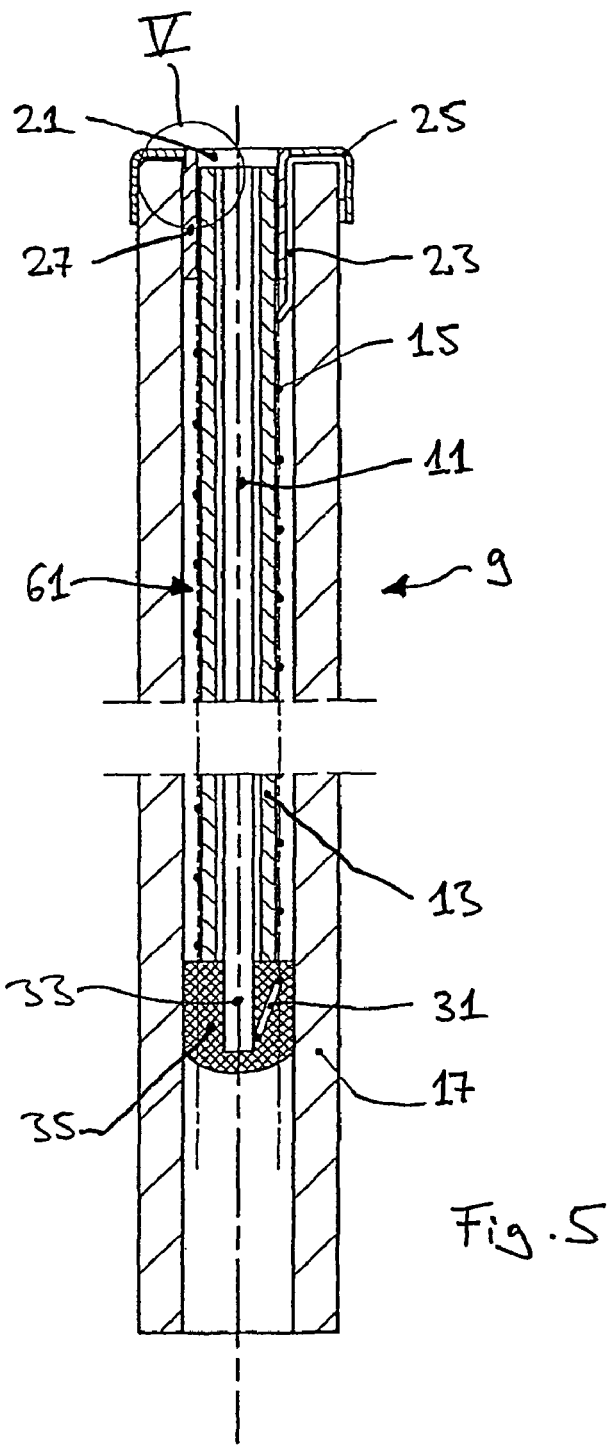
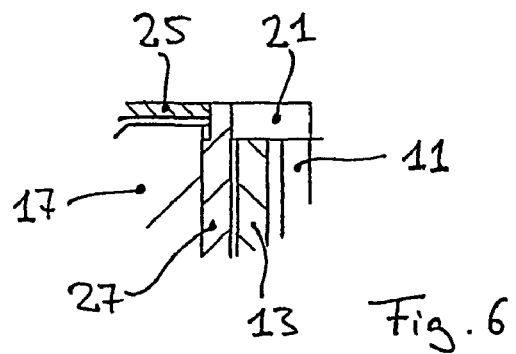
Fig. 5
Fig. 6

INHALATION UNIT

FIELD OF THE INVENTION

The invention relates to a mobile inhalation unit for the inhalation of active agents, comprising a heating device which has a thermal reservoir for the heating of air which flows along the thermal reservoir, with the thermal reservoir being able to be heated by means of a heating wire of the heating device.

An inhalation unit of this type allows the inhalation of active agents, in particular of medical drugs and/or aromas. The user of such an inhalation unit sucks in air which first flows along the thermal reservoir and is hereby heated. Then the heated air flows along an active agent depot, with active agents located in the active agent depot being released by the heated air, being taken up by the heated air and finally being inhaled by the user.

BACKGROUND OF THE INVENTION

A smoke-free cigarette is known from WO 2004/098324 A2. It has a replaceable piece (nicotine depot), a reusable piece with a sleeve and a heating device as well as a storage and charging station having an accumulator and a thermostat. The heating device of the reusable piece has a heating spiral and a heat-storing medium, with airflow passages being provided between the heat-storing medium and the sleeve. The reusable piece can be received in the storage and charging station for the purpose of heating, with the heating spiral of the reusable part been heated for so long until the thermostat ends the heating process.

An ideal heat transfer to the thermal reservoir and a precise reaching of the desired temperature are not always ensured by ending the heating process on the basis of a corresponding signal of a thermostat.

A mobile inhalation unit is known from EP-A-0 430 559 in which an active agent depot is maintained at a relatively constant operating temperature.

U.S. Pat. No. 5,878,752 describes a mobile inhalation unit having a heating spiral which is used for cleaning purposes.

SUMMARY OF THE INVENTION

It is an object of the invention to improve the heating of the thermal reservoir of a heating device in an inhalation unit of the explained type.

This object is satisfied by an inhalation device having the features of claim 1.

The heating wire of the heating device has a high temperature coefficient. A simple and reliable determination of the instantaneous temperature of the thermal reservoir is thereby possible, as will be explained in the following, without additional temperature probes being required in the thermal reservoir. The heating wire itself rather serves as a temperature sensor ("thermal feedback").

The ratio of the relative change in the electrical resistance to the temperature change in accordance with the following formula is called the temperature coefficient ($\alpha$):

$$\alpha = \frac{\Delta R}{R \cdot \Delta T},$$

where $\Delta R$ is the change in the resistance (or in the specific resistance), R is the resistance (or specific resistance) and $\Delta T$ is the change in temperature. The temperature coefficient therefore characterizes the dependence of the resistance R on the temperature T.

In contrast, the heating wires in known heating devices have a comparatively low temperature coefficient to obtain a low dependence of the electrical resistance of the heating wire on the temperature and thus a substantially temperature-independent heating power. The alloy konstantan, for example, has a temperature coefficient of approx. $0.00004$ $K^{-1}$.

To heat the heating wire, electrical energy, that is an electrical current of a specific amount, is supplied to it. In order simultaneously to determine the instantaneous temperature of the thermal reservoir or of the heating wire, the instantaneous value of the electrical resistance of the heating wire is measured. The measured result can be used to control the further supply of the electrical energy on the basis of the resistance determined, that is, for example, to decrease or increase the current or to completely switch off the energy supply. Due to the high temperature coefficient of the heating wire (high gradient of the R/T curve), the instantaneous temperature of the heating wire can be determined with high accuracy from the measured resistance without additional temperature sensors being necessary.

The precise observation of a predetermined temperature of the heating wire and thus of the thermal reservoir is particularly important in the inhalation of medical active agents so that the designated dosage is reliably reached, on the one hand, and is in turn not excessively exceeded, on the other hand. A precise temperature determination and a correspondingly precise control or feedback control of the heating power is also particularly important for mobile applications of the inhalation unit since the capacity of the electrical energy source used (accumulator) is limited and should always be utilized to an optimum.

A particularly advantageous value of the temperature coefficient lies, for example, at $0.003$ $K^{-1}$, with a better measuring resolution naturally being achieved, the higher the temperature coefficient is.

The mobile inhalation can furthermore have an electrical energy source which can be connected to the heating wire and an evaluation and control circuit by which the electrical resistance of the heating wire can be determined and by which the electrical energy supplied to the heating wire can be set with reference to the resistance determined.

Further embodiments of the invention are described in the dependent claims.

BRIEF DESCRIPTION OF THE DRAWINGS

The invention will be described in the following only by way of example with reference to the drawings.

FIG. 1 shows a perspective view of a heating device;

FIG. 2 shows a perspective view of parts of the heating device;

FIG. 5 shows the heating device in a longitudinal section;

FIG. 6 is a detailed view of the region VI of FIG. 5;

DETAILED DESCRIPTION OF THE PREFERRED EMBODIMENTS

Figure 3:
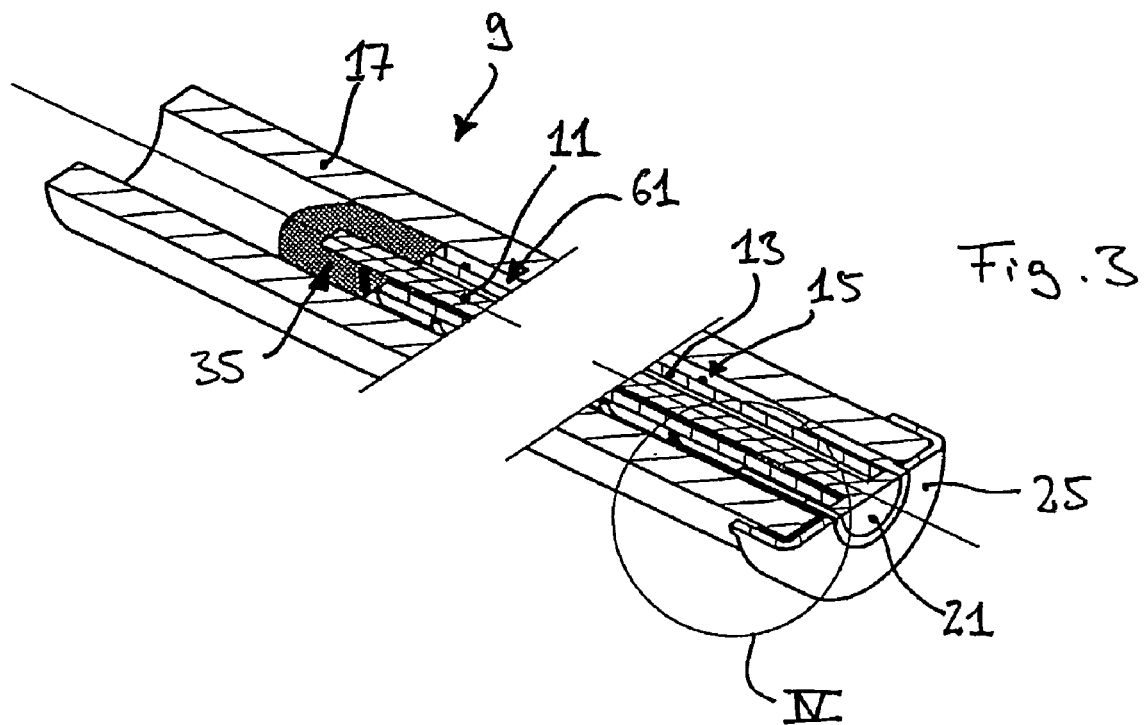
FIG. 3 shows a cut-away perspective view of the heating device.
Figure 4:
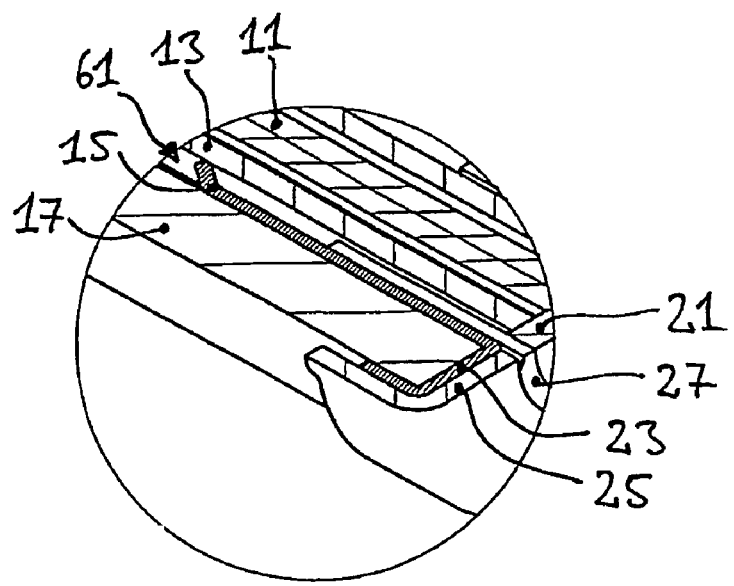
FIG. 4 is a detailed view of the region IV of FIG. 3.

The heating device 9 shown in FIGS. 1 to 6 has an elongate shape with an almost rotationally symmetrical design. The heating device 9 has—radially from the inside to the outside—a center contact pin 11, a ceramic inner tube 13, a heating spiral 15 and a ceramic outer tube 17 (cf. in particular FIGS. 3 and 5). The center contact pin 11, the inner tube 13, the heating spiral 15 and the outer tube 17 are arranged coaxially to one another. The center contact pin 11 has a high electrical conductivity and comprises, for example, copper-nickel or other metal alloys.

Figure 8:
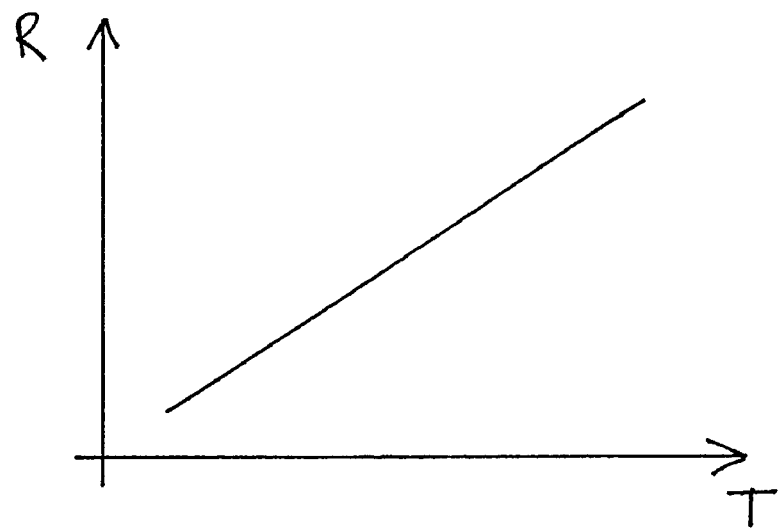
FIG. 8 shows the dependence of the resistance of the heating spiral on the temperature.

The heating spiral 15, in contrast, has a high electrical resistance. It serves for the heating of the inner tube 13 and of the outer tube 17 and has a high temperature coefficient, as will be explained in the following (FIG. 8). The heating spiral 15 can, for example, comprise the nickel-iron alloy "Resistherm" (registered trademark) with the components aluminum (mass portion 0.6%), chromium (0.3%), iron (30%), manganese (0.5%) and nickel (rest), with a temperature coefficient of approx. 0.003 K−1. The inner tube 13 and the outer tube 17 together form a thermal reservoir for the heat output by the heating spiral and they comprise a ceramic material, for example titanate or steatite.

A disk-shaped contact socket 21 is shaped at a front-side end of the center contact pin 11 (at the right in FIG. 3, at the top in FIG. 5). The front side of the ceramic inner tube 13 contacts the rear side of this contact socket 21. A front-side connector end 23 of the heating spiral 15 is bent over in U shape, with the U shape engaging around the front side of the ceramic outer tube 17 (cf. FIGS. 2 and 3). A ring contact 25 of copper or of a metal alloy with a conductive covering is placed onto the front-side end of the outer tube 17 by press-fitting such that the front-side connector end 23 of the heating spiral 15 contacts the inner side of the ring contact 25 and thus an electrical connection is established between these two parts.

An insulator sleeve 27 which electrically insulates the contact socket 21 and the ring contact 25 from one another is arranged between the front-side end of the center contact pin 11 with the contact socket 21 and the front-side end of the ceramic inner tube 13, on the one hand, and the front-side end of the ceramic outer tube 17 with the ring contact 25 placed on, on the other hand. In the embodiment shown, the contact socket 21, the insulator sleeve 27 and the ring contact 25 terminate flush with one another at the front side of the heating device 9 (cf. FIGS. 3 and 5). The contact socket 21, the insulator sleeve 27 and the ring contact 25 are arranged coaxially to one another.

A rear-side connector end 31 of the heating spiral 15 is electrically connected to a rear-side end 33 of the center contact pin 11. This rear-side end 33 of the center contact pin 11 projects out of the ceramic inner tube 13 which is shorter than the center contact pin 11 and shorter than the ceramic outer tube 17. The rear-side end 33 of the center contact pin 11 and the rear-side connector end 31 of the heating spiral 15 are fixed to the inner side of the ceramic outer tube 17 by means of a fastening mass 35. The fastening mass 35 can, for example, be a cement which is cast into the inner space of the outer tube 17 from the rear side. The ceramic inner tube 13 is captured between the fastening mass 35, on the one hand, and the contact socket 21 of the center contact pin 11, on the other hand.

The heating device 9 shown in FIGS. 1 to 6 is provided for use in a mobile inhalation unit for the inhalation of active agents, with air flowing past the heating device 9 being heated and active agents which can then be inhaled being released from an active agent depot.

Figure 7:
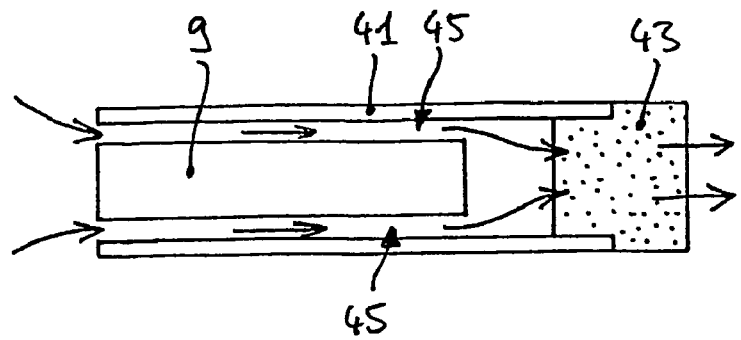
FIG. 7 shows a mobile inhalation unit with the heating device.

FIG. 7 shows parts of such a mobile inhalation unit in a schematic cross-sectional view. This inhalation unit has a connection sleeve 41 which surrounds the heating device 9 peripherally and is connected at one end to an air-permeable active agent depot 43. One or more flow passages 45 are formed between the connection sleeve 41 and the heating device 9. The user of the inhalation unit fixes his mouth on the active agent depot 43 and sucks in air. The sucked in air flows through the flow passages 45 along the heating device 9 (cf. arrows in FIG. 7). The air thus flows along the ceramic outer tube 17 (FIGS. 1, 3, 5) which has previously been heated by means of the heating spiral 15. The thus heated air then flows through the active agent depot 43, heats it and thereby releases active agents stored in the active agent depot 43 which are taken up by the air and are taken along. The user therefore now inhales these active ingredients.

It is important for many applications of such an inhalation unit that the active agents are released in a predetermined amount and/or as uniformly as possible during a predetermined period. It is in turn important for this purpose that the temperature of the heating spiral 15, with which the thermal reservoir (inner tube 13 and outer tube 17) is heated, can be set as precisely as possible. It is therefore desirable for the actual instantaneous temperature of the heating spiral 15 to be able to be determined.

Provision is made for this purpose for the heating spiral 15 to comprise a material which—as already mentioned—has a high temperature coefficient, i.e. the electrical resistance of the heating spiral 15 depends largely on its temperature. FIG. 8 shows by way of example such a dependence of the resistance R of the heating spiral 15 on its temperature T. The high gradient of the graph shown in FIG. 8 is characteristic for the material of the heating spiral 15 to be used. The corresponding temperature value can be determined with high accuracy from a determined resistance value on the basis of the high temperature dependence of the resistance.

Figure 9:
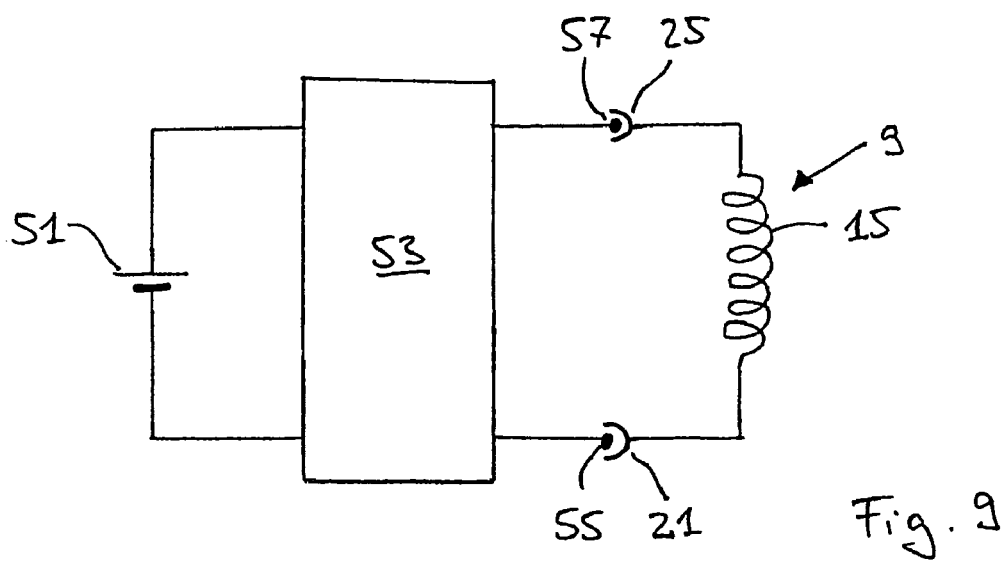
FIG. 9 shows a block diagram of the wiring of a heating wire and of an electrical energy source with an evaluation and control circuit.

FIG. 9 shows further parts of the already described mobile inhalation device. It has an accumulator 51 or a battery as an electrical energy source as well as an evaluation and control circuit 53 which is connected to the two poles of the accumulator 51. The evaluation and control circuit 53 has two connection contacts 55, 57 at the output side. The evaluation and control circuit 53 serves as a driver for the energy supply from the accumulator 51 to the heating spiral 15. The heating device 9, of which only the heating spiral 15 is shown in FIG. 9, is connected at times to the connection contacts 55, 57 by means of the contact socket 21 and the ring contact 25, with an electrical current being led through the heating spiral 15 to heat it.

The evaluation and control circuit 53 controls the current which is led through the heating spiral 15 in dependence on the temperature of the heating spiral 15. For this purpose, the evaluation and control circuit 53 measures the electrical resistance R of the heating spiral 15. Due to the high temperature dependence of the resistance R (cf. FIG. 8), the temperature T results from it with high accuracy.

In the following, advantages of the heating device in accordance with FIGS. 1 to 6 and of the inhalation unit in accordance with FIGS. 7 and 9 will be explained which can each be realized per se or in combination with one another:
a) The thermal reservoir has both an outer part (outer tube 17) arranged outside the heating spiral 15 and an inner part (inner tube 13) arranged inside the heating spiral 15. A uniform heat output over a long time period is hereby made possible by means of the heating spiral 15 after the heating of the thermal reservoir and the heat output proves to be less sensitive to different ambient temperatures of the thermal reservoir.

b) In accordance with a further development of the aforesaid embodiment, it is preferred for the heating spiral 15 to contact the outer side of the inner part of the thermal reservoir (inner tube 13) and for an air gap 61 to be provided at least along a longitudinal section of the heating device 9 between the heating spiral 15 and the inner side of the outer part of the thermal reservoir (outer tube 17) (cf. FIG. 5). An air gap 61 of this type likewise contributes to the improvement of the uniformity of the heat output. The heat transfer from the heating spiral 15 to the outer tube 17 is namely worse than to the inner tube 13 due to the air gap 61. After the interruption of the energy supply of the heating spiral 15, this has the consequence that the heat output from the inner tube 13 to the outer tube 17 is delayed and the inner tube 13 acts as a thermal reservoir at a higher temperature level for the outer tube 17. While the outer tube 17 outputs heat to the outside, the inner tube 13 can thus "reheat" the outer tube 17 longer.

c) Since the rear-side connector end 31 of the heating spiral 15, the rear-side end 33 of the center contact pin 11 and thus also the rear-side end of the inner tube 13 are together fixed in position by means of the fastening mass 35, the heating device 9—in a substantially unchanged manufacturing process—can also be produced in an embodiment in which the contact socket 21 of the center contact pin 11 is offset with respect to the front side of the outer tube 17 and thus with respect to the ring contact 25. In other words, alternatively to the embodiment shown in FIGS. 3 and 5, a pin engagement contact can be realized by which an electrical short-circuit at the energy source used can be avoided more reliably. A pin engagement contact of this type is not required or desired in all cases. A particular advantage of the explained aspect of the heating device 9, however, consists of the fact that both variants (flush or offset contact socket 21) can be realized with substantially the same manufacturing process.

d) The contact socket 21 and the ring contact 25 have a rotationally symmetrical design (cf. FIG. 1). A connection to the electrical energy source used is hereby possible in any desired angular position of the heating device 9, which improves the operating comfort for the user.

e) The evaluation and control circuit 53 (FIG. 9) can be configured for a feedback control of the energy supply to the heating spiral 15, with the electrical energy supplied to the heating spiral 15 being set in accordance with a predetermined time development of the temperature T (or of the resistance R) of the heating spiral 15. In other words, provision is not only made for the heating of the heating spiral 15 to be ended on the reaching of a predetermined temperature, but provision is also made for the heating process to follow a predetermined time development. The utilization of the capacity of the accumulator 51 can hereby be optimized.

The invention claimed is:

1. A mobile inhalation unit for the inhalation of active agents, comprising a heating device (9) and a connection sleeve (41) which surrounds the heating device (9) peripherally and is connected or can be connected at one end to an air-permeable active agent depot (43), wherein at least one flow passage (45) is configured between the connection sleeve (41) and the heating device (9), wherein the heating device (9) has a heating wire configured as a heating spiral (15) and having two connector ends (23, 31) for the supply of electrical energy, and wherein the heating device (9) has a thermal reservoir (13, 17) for the heating of air which flows along the thermal reservoir, with the thermal reservoir being able to be heated by means of the heating wire, wherein the heating wire (15) has a temperature coefficient of at least 0.001 $K^{-1}$, wherein a cylindrical hollow outer part (17) of the thermal reservoir is arranged outside the heating spiral and a cylindrical hollow inner part (13) of the thermal reservoir is arranged inside the heating spiral, said inner part being separate from said outer part, and wherein air sucked in by a user through the at least one flow passage (45) flows along the total length of the outer part (17) of the thermal reservoir.

2. An inhalation unit in accordance with claim 1, characterized in that the heating wire (15) has a temperature coefficient of approx. 0.003 $K^{-1}$.

3. An inhalation unit in accordance with claim 1, characterized in that the heating wire (15) comprises a nickel-iron alloy.

4. An inhalation unit in accordance with claim 1, characterized in that the heating spiral (15) extends along the longitudinal axis of the hollow cylindrical thermal reservoir (17), with a first connector end (23) of the heating spiral (15) being arranged at or adjacent to a first end of the hollow cylindrical thermal reservoir (17) and a second connector end (31) of the heating spiral (15) being arranged at or adjacent to a second end of the hollow cylindrical thermal reservoir (17); and in that the heating device further has a center contact pin (11) which is arranged inside the hollow cylindrical thermal reservoir (17), whose first end (21) is arranged at or adjacent to the first end of the hollow cylindrical thermal reservoir (17) and whose second end (33) is arranged at or adjacent to the hollow cylindrical thermal reservoir (17), with the second end (33) of the center contact pin (11) being electrically connected to the second connector end (31) of the heating spiral (15) and being fastened to the inner side of the hollow cylindrical thermal reservoir (17).

5. An inhalation unit in accordance with claim 4, characterized in that a connector end (23) of the heating wire (15) has a ring contact which surrounds an end (21) of the center contact pin (11) coaxially to the center contact pin.

6. An inhalation unit in accordance with claim 1, characterized in that the outer part (17) and the inner part (13) of the thermal reservoir are arranged coaxially to one another.

7. An inhalation unit in accordance with claim 1, characterized in that the heating spiral (15) contacts the outer side of the inner part (13) of the thermal reservoir; and in that an air gap (61) is provided at least sectionally between the heating spiral (15) and the inner side of the outer part (17) of the thermal reservoir.

8. An inhalation unit in accordance with claim 1, characterized in that the thermal reservoir or reservoirs (13, 17) comprise a ceramic material.

9. An inhalation unit in accordance with claim 1, characterized by an electrical energy source (51) which is connectable to the heating wire (15), and by an evaluation and control circuit (53) by which the electrical resistance (R) of the heating wire (15) can be determined and by which the electrical energy supplied to the heating wire can be set with reference to the determined resistance.

10. An inhalation unit in accordance with claim 1, characterized in that the inhalation unit has the active agent depot (43), with the active agent depot (43) being arranged adjacent to the thermal reservoir (13, 17) of the heating device (9) such that the air flowing along the thermal reservoir and hereby being heated is guided along the active agent depot to take up active agents located in the active agent depot.

11. A mobile inhalation unit for the inhalation of active agents, comprising a heating device (9) and a connection sleeve (41) which surrounds the heating device (9) peripherally and is connected or can be connected at one end to an air-permeable active agent depot (43), wherein at least one flow passage (45) is configured between the connection sleeve (41) and the heating device (9), wherein the heating device (9) has a heating wire configured as a heating spiral (15) and having two connector ends (23, 31) for the supply of electrical energy, and wherein the heating device (9) has a thermal reservoir (13, 17) for the heating of air which flows along the thermal reservoir, with the thermal reservoir being able to be heated by means of the heating wire, wherein the heating wire (15) has a temperature coefficient of at least $0.001\ K^{-1}$, wherein an outer part (17) of the thermal reservoir is arranged outside the heating spiral and an inner part (13) of the thermal reservoir is arranged inside the heating spiral, and wherein air sucked in by a user through the at least one flow passage (45) flows along the total length of the outer part (17) of the thermal reservoir, wherein at least the outer part (17) of the thermal reservoir is hollow cylindrical; in that the heating spiral (15) extends along the longitudinal axis of the hollow cylindrical thermal reservoir (17), with a first connector end (23) of the heating spiral (15) being arranged at or adjacent to a first end of the hollow cylindrical thermal reservoir (17) and a second connector end (31) of the heating spiral (15) being arranged at or adjacent to a second end of the hollow cylindrical thermal reservoir (17); and in that the heating device further has a center contact pin (11) which is arranged inside the hollow cylindrical thermal reservoir (17), whose first end (21) is arranged at or adjacent to the first end of the hollow cylindrical thermal reservoir (17) and whose second end (33) is arranged at or adjacent to the hollow cylindrical thermal reservoir (17), with the second end (33) of the center contact pin (11) being electrically connected to the second connector end (31) of the heating spiral (15) and being fastened to the inner side of the hollow cylindrical thermal reservoir (17).

12. An inhalation unit in accordance with claim 11, characterized in that the heating wire (15) has a temperature coefficient of approx. $0.003\ K^{-1}$.

13. An inhalation unit in accordance with claim 11, characterized in that the heating wire (15) comprises a nickel-iron alloy.

14. An inhalation unit in accordance with claim 11, characterized in that a connector end (23) of the heating wire (15) has a ring contact which surrounds an end (21) of the center contact pin (11) coaxially to the center contact pin.

15. An inhalation unit in accordance with claim 11, characterized in that the inner part is hollow and cylindrical and that the outer part (17) and the inner part (13) are arranged coaxially to one another.

16. An inhalation unit in accordance with claim 11, characterized in that the heating spiral (15) contacts the outer side of the inner part (13) of the thermal reservoir; and in that an air gap (61) is provided at least sectionally between the heating spiral (15) and the inner side of the outer part (17) of the thermal reservoir.

17. An inhalation unit in accordance with claim 11, characterized in that the thermal reservoir or reservoirs (13, 17) comprise a ceramic material.

18. An inhalation unit in accordance with claim 11, characterized by an electrical energy source (51) which is connectable to the heating wire (15), and by an evaluation and control circuit (53) by which the electrical resistance (R) of the heating wire (15) can be determined and by which the electrical energy supplied to the heating wire can be set with reference to the determined resistance.

19. An inhalation unit in accordance with claim 11, characterized in that the inhalation unit has the active agent depot (43), with the active agent depot (43) being arranged adjacent to the thermal reservoir (13, 17) of the heating device (9) such that the air flowing along the thermal reservoir and hereby being heated is guided along the active agent depot to take up active agents located in the active agent depot.

* * * * *